(12) United States Patent
Coker et al.

(10) Patent No.: US 7,843,566 B2
(45) Date of Patent: Nov. 30, 2010

(54) DEVICE FOR DETECTION AND MEASUREMENT OF A TARGET COMPOUND SUCH AS A FOOD TOXIN

(75) Inventors: Raymond Douglas Coker, Bromley Kent (GB); Martin Jesse Nagler, Chatham Kent (GB); Michael Paul Andreou, Horsham West Sussex (GB)

(73) Assignee: University of Greenwich, London (GB)

( * ) Notice: Subject to any disclaimer, the term of this patent is extended or adjusted under 35 U.S.C. 154(b) by 0 days.

(21) Appl. No.: 11/914,841

(22) PCT Filed: May 19, 2006

(86) PCT No.: PCT/GB2006/050115
§ 371 (c)(1),
(2), (4) Date: Mar. 13, 2008

(87) PCT Pub. No.: WO2006/123189
PCT Pub. Date: Nov. 23, 2006

(65) Prior Publication Data
US 2008/0198379 A1    Aug. 21, 2008

(30) Foreign Application Priority Data
May 20, 2005   (GB)   .................................. 0510362.7

(51) Int. Cl.
*G01N 21/25* (2006.01)
(52) U.S. Cl. ..................................................... 356/417
(58) Field of Classification Search ................. 356/317; 435/7.1, 7.2, 7.9, 29, 34
See application file for complete search history.

(56) References Cited

U.S. PATENT DOCUMENTS

| 5,178,832 A | 1/1993 | Phillips et al. |
| 5,989,835 A * | 11/1999 | Dunlay et al. ................. 506/10 |
| 6,637,438 B1 | 10/2003 | Lane |
| 2001/0046712 A1 * | 11/2001 | Hang et al. .................. 436/172 |
| 2003/0127609 A1 * | 7/2003 | El-Hage et al. .............. 250/574 |
| 2004/0029210 A1 * | 2/2004 | Robillot et al. ............... 435/29 |
| 2006/0029941 A1 | 2/2006 | Koo et al. |
| 2006/0046313 A1 | 3/2006 | Roth et al. |
| 2006/0146317 A1 * | 7/2006 | Aklian ....................... 356/128 |

FOREIGN PATENT DOCUMENTS

EP    1533607    6/2005

(Continued)

*Primary Examiner*—Gregory J Toatley
*Assistant Examiner*—Abdullahi Nur
(74) *Attorney, Agent, or Firm*—Occhiuti Rohlicek & Tsao LLP

(57) ABSTRACT

Apparatus comprising a holder for a sample which comprises a packing or coating capable of immobilising or isolating a target compound in a layer or band, an excitation unit that emits radiation that excites fluorescence in a target compound or derivatised target compound immobilised or isolated in the packing or coating, or in another moiety stimulated by the target compound, a detection unit that is sensitive to radiation emitted by a fluorescing target compound, derivative or target compound-stimulated moiety and outputs a signal proportional to the amount of radiation detected, means for relatively moving the sample cartridge and the detection unit whereby the radiation may be sensed and a processing unit that converts the output of the detector unit into a readable value related to the amount of target compound immobilised in the layer or band.

35 Claims, 9 Drawing Sheets

FOREIGN PATENT DOCUMENTS

| | | |
|---|---|---|
| EP | 0956497 | 8/2005 |
| EP | 1592812 | 4/2009 |
| WO | WO89/03037 | 4/1989 |
| WO | WO01/28367 | 4/2001 |
| WO | WO02/23196 | 3/2002 |
| WO | WO02/065115 | 8/2002 |
| WO | WO2004/090505 | 10/2004 |
| WO | WO2006/123189 | 11/2006 |
| WO | WO2007/078635 | 7/2007 |

* cited by examiner

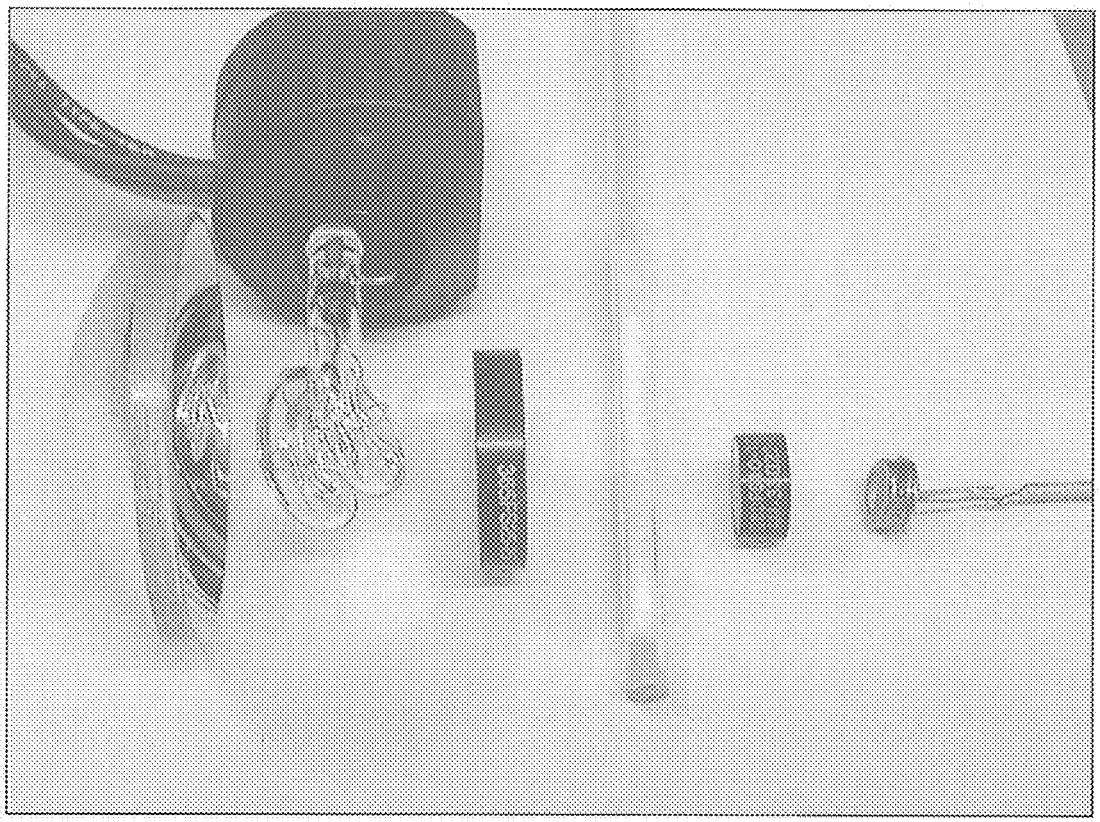
Fig. 2 Optical Components

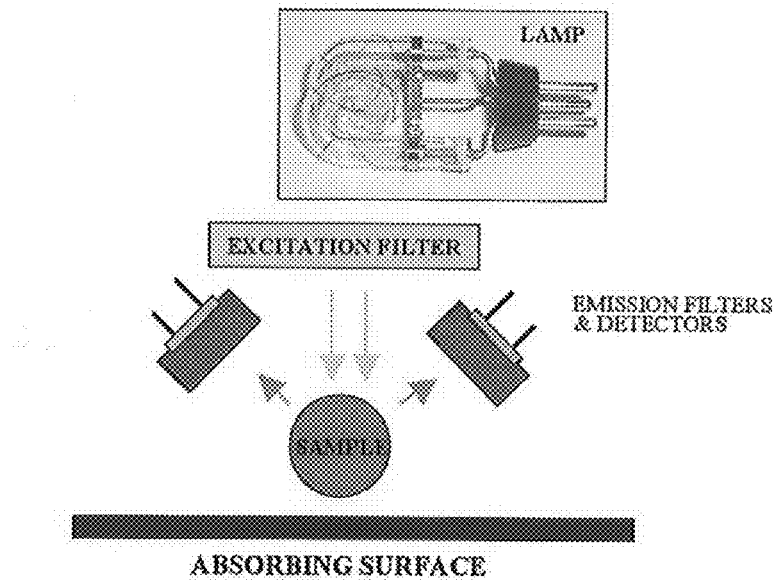
Fig. 3 Top View of Exciter/Detector arrangement
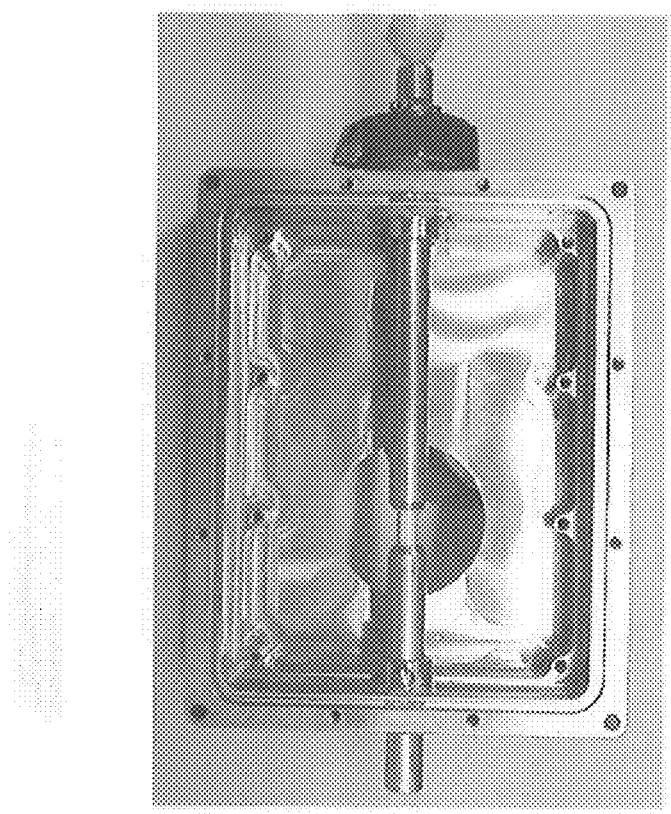
Fig. 4 Mini-column in holder

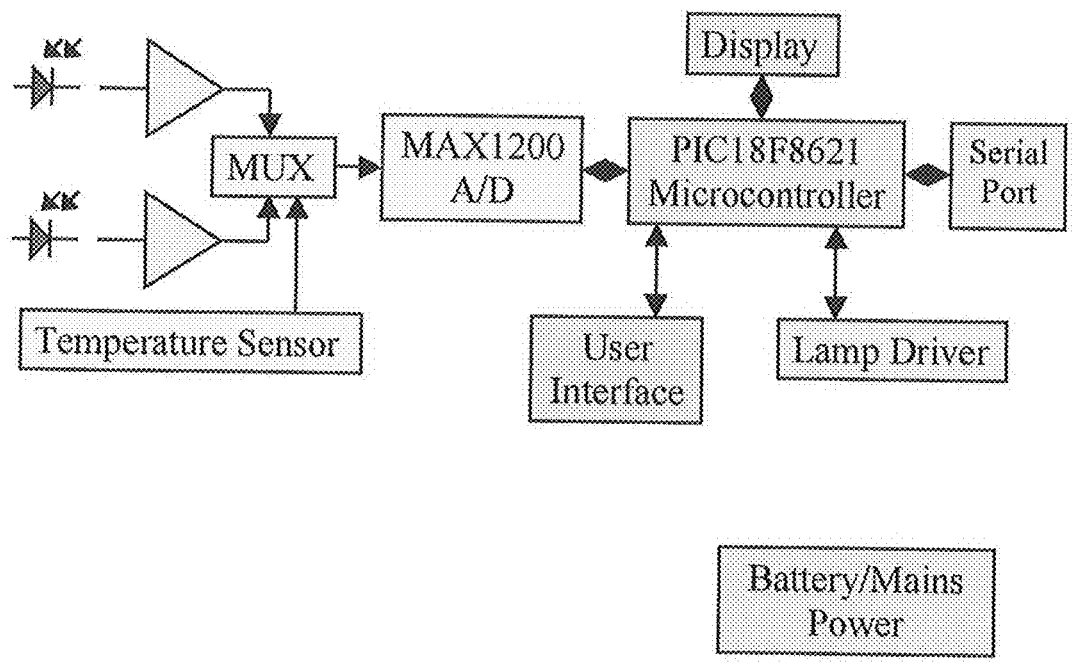
Fig. 5  BLOCK DIAGRAM OF ELECTRONICS
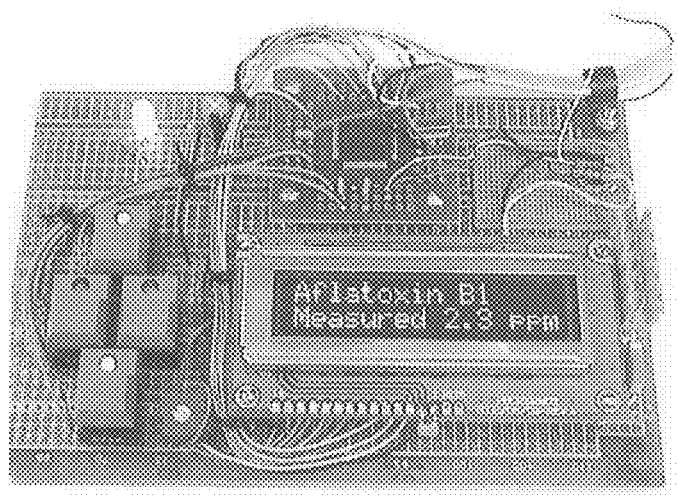
Fig. 6  PROCESSING UNIT

DEVICE FOR DETECTION AND MEASUREMENT OF A TARGET COMPOUND SUCH AS A FOOD TOXIN

CROSS-REFERENCE TO RELATED APPLICATIONS

This application is the National Stage of International Application No. PCT/GB2006/050115, filed on May 19, 2006, which claims the benefit of European Application No. 0510362.7, filed on May 20, 2005. The contents of both applications are hereby incorporated by reference in their entirety.

FIELD OF THE INVENTION

The present invention relates to apparatus for the detection, and measurement of target compounds such as food toxins such as mycotoxins, such as aflatoxins. The device finds its primary use for detection of mycotoxins in foodstuffs, but may also be used for detection of other toxins and even non-toxic compounds of interest.

BACKGROUND OF THE INVENTION

Mycotoxins are toxic metabolic by-products of fungi which can dangerously contaminate a wide variety of human foods and animal feeds, including edible nuts, oilseeds, cereal grains, and forages and products derived from them. Among the most significant are aflatoxins, a group of closely-related mycotoxins produced by the fungi *Aspergillus flavus* and *A. parasiticus*. Not all isolates of the fungus produce aflatoxins; thus, the mere presence of *A. flavus* or *A. parasiticus* does not mean that aflatoxins will be present in the substrate. Accordingly direct determination of mycotoxin level is an important aspect of quality control in foods and feeds.

Such measurements have conventionally been carried out by the use of high performance liquid chromatography (HPLC). However in those cases where HPLC equipment is not available or appropriate, determination by thin layer chromatography (TLC) is also possible. Commercial scanners are available for mycotoxin determination after TLC separation, using mercury lamps with an emission wavelength of 366 nm as a light source to stimulate fluorescence, which is detected and quantified by photo-multipliers.

For quantitative testing there are also radioimmunoassay techniques and immunochemically-based techniques such as enzyme-linked immunosorbent assay (ELISA) methods.

Qualitative detection of mycotoxins can be carried out using small chromatographic columns (traditionally called 'minicolumns'). Various minicolumn methods have been adopted as official tests of the AOAC International (Association of Official Analytical Communities). The major uses of minicolumn tests for aflatoxin are as "go" or "no go" field tests to accept or reject for example a truckload of peanuts or corn, and as central laboratory screening tests to avoid the need to quantitatively test samples that do not contain a detectable amount of aflatoxin.

SUMMARY OF THE INVENTION

According to a first aspect, the present invention provides apparatus for the detection or determination of a target compound comprising a target compound, a derivatised target compound or target compound-stimulated moiety, said apparatus comprising: means for mounting a sample cartridge, which sample cartridge comprises a packing or coating capable of immobilising or isolating the target in a layer or band, an excitation unit for emitting radiation that excites fluorescent radiation, a detection unit that is sensitive to said fluorescent radiation, and means for relatively moving the mounting means and the detection unit whereby the fluorescent radiation from the target may be sensed.

In one arrangement, said target obscures said emitted fluorescent radiation.

Thus, a fluorophore—a fluorescent moiety—is incorporated into a polymer in the cartridge and the amount of fluorescence quenching, which is caused by the target compound adsorbed onto the polymer, is measured. The amount of quenching is proportional to the amount of target compound.

In another arrangement, said excitation unit is adapted to emit radiation that excites fluorescence in a target immobilised or isolated in the packing or coating, a detection unit that is sensitive to radiation emitted by the fluorescing target, and said means for relatively moving the mounting means and the detection unit allows the fluorescence from the target to be sensed.

The present invention also provides apparatus for the detection or determination of a target compound such as food toxins such as mycotoxins comprising:

a holder for a sample cartridge which comprises a packing or coating capable of immobilising or isolating a target compound in a layer or band, an excitation unit that emits radiation that excites fluorescence in a target compound or derivatised target compound immobilised or isolated in the packing or coating, or in another moiety stimulated by the target compound, a detection unit that is sensitive to radiation emitted by a fluorescing target compound, derivative or target compound-stimulated moiety, and, means for relatively moving the sample cartridge and the detection unit whereby the radiation may be sensed.

The means for relatively moving the mounting means and the detection unit may comprise means for relatively moving them in a linear (such as an axial) direction and means for relatively rotating them.

The means for relatively moving the mounting means and the detection unit may comprise a screw-threaded rod which is driven by an actuator motor.

Alternatively, the means for relatively moving the mounting means and the detection unit may comprises a first stepper motor for relatively moving them in a linear direction and a second stepper motor for relatively rotating them.

By such movement, the extent of the fluorescing target may be determined and also the total fluorescence emitted. In this way, the amount of the target material may be determined, particularly after a calibrating step with a known quantity of the target material.

In this way, it is possible to simply measure the presence and quantity of the target material (e.g. toxin) present.

Preferably the detection unit outputs a signal proportional to the amount of radiation detected, so that the detected toxin can be quantified.

Accordingly in a preferred embodiment the device also comprises a processing unit that converts the output of the detector unit into a readable value related to the amount of target compound immobilised in the layer or band.

The term 'cartridge' is used herein to include any removable unit capable of supporting a packing or coating of adsorbent on which a layer of toxin can be immobilised. Suitable 'cartridges' include small glass or plastics tubes ("mini-columns") containing suitable mineral or polymer adsorbent packings, and cuvettes or rods with internal or external coatings of adsorbent.

Typically the excitation unit comprises a light source and an excitation filter and the the detection unit comprises a photodiode and an emission filter, both with suitable optical systems.

Preferably the above components are mounted on a common staging and/or incorporated in a housing so that the device can be handled as a unitary assembly.

BRIEF DESCRIPTION OF THE DRAWINGS

Preferred embodiments of the invention will now be described with reference to the accompanying drawings in which:

FIG. 2 is a view of optical components used in one embodiment of a device;

FIG. 3 is a schematic top view of an excitation/detection arrangement for use in conjunction with the components of FIG. 2;

FIG. 4 is a view of a mini-column in a holder for use in the arrangement of FIG. 3;

FIG. 5 is schematic block diagram of the electronics of a detector and processing unit for use in the arrangement of FIG. 3;

FIG. 6 is an overhead view of an assembled processing unit based on FIG. 5;

DETAILED DESCRIPTION OF THE PREFERRED EMBODIMENTS OF THE INVENTION

The device is based on the knowledge that radiation of certain wavelengths excites certain food components or contaminants such as mycotoxins to fluoresce, and that the wavelength of the emitted fluorescent light is significantly different (usually longer) than the excitation wavelength. On the assumption that the amount of light emitted is proportional to the amount of the substance, a measurement of the amount of light emitted can be used to quantify the amount of target compound, such as a mycotoxin, immobilised in the sample cartridge.

Figure 1:
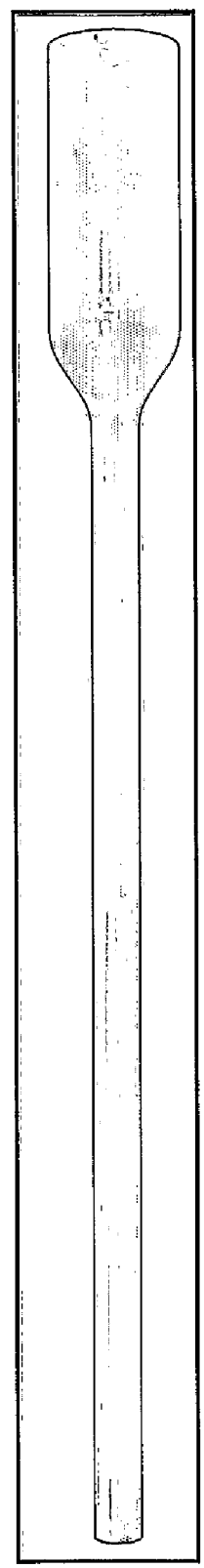
FIG. 1 is a side view of a typical mini-column for immobilising a food toxin.

Operating the device involves the extraction of a target such as a chemical toxin from food, the immobilisation of the toxin as a layer or band in a columnar packing or coating, the illumination of the band, typically with UV radiation, at an appropriate wavelength to excite the emission of fluorescent light by the band, the detection of the fluorescence and the conversion of the detected signal into a direct measurement of the concentration of the toxin (typically in parts per billion).

Accordingly the device typically comprises a holder for a sample cartridge (e.g. mini-column, cuvette or rod) which comprises a packing or coating capable of immobilising or isolating a target compound in a layer or band, an excitation unit that emits radiation that excites fluorescence in a target compound or derivatised target compound immobilised or isolated in the packing or coating, or in another moiety stimulated by the target compound, a detection unit that is sensitive to radiation emitted by a fluorescing target compound, derivative or target compound-stimulated moiety and outputs a signal proportional to the amount of radiation detected, means for relatively moving the sample cartridge and the detection unit whereby the radiation may be sensed. and a processing unit that converts the output of the detector unit into a readable value related to the amount of target compound immobilised in the layer or band. The output may be fed to a computer for analysis or to an associated display screen. The relative movement of the sample cartridge and the detection unit doesn't just allow the radiation to be sensed by relatively aligning them but allows the fluorescing target compound to be scanned thereby ensuring that the extent of the fluorescing target compound is detected to give a quantitative measure of the amount of fluorescing target compound present.

Typically the housing also contains a power source, or means for connecting to a power source, to power the excitation unit, the detection unit and the processing unit.

A typical 'cartridge' for use in the device is a so-called mini-column, which comprise transparent tubes packed with isolated layer(s) of mineral adsorbent(s). In use, a solution extracted from a sample potentially contaminated with mycotoxins is passed through the detector tube or is transported through the tube by a suitable solvent or solvent mixture. The essence of the mini-column system is that a mycotoxin of interest is immobilised by a specific adsorbent so that the mycotoxin is present in the mini-column as a layer or band which can be detected by fluorescence. Some mycotoxins are naturally fluorescent, whereas others require the addition of a derivatising agent to the solution or to the column in order to produce a fluorescent derivative.

As the mycotoxin mixture passes through the device and is contacted by the various mineral adsorbents, selected mycotoxins are immobilized on a specific mineral. The mini-column may be set up to detect a single mycotoxin. Alternatively the mini-column may be set up so that other mycotoxins pass through that layer to be immobilized on subsequent downstream mineral layers. If the mycotoxins for which the device is specific are present above the detection limit in the sample, they will appear as fluorescent bands within the mineral layers which are selective for those particular mycotoxins when the developed detector tube is exposed to UV radiation. For some mycotoxins, specially treated minerals may be employed as adsorbents to generate fluorescence. Additional layers in the column may be used to 'clean-up' the solution of mycotoxin to remove substances that could interfere with the detection process.

Published AOAC standard tests routines include pre-test clean-up protocols for preparation of the solution prior to use of the mini-column. The sample extract may be cleaned-up by solid phase extraction (SPE) using cartridges containing adsorbents which trap the toxin but allow passage of interfering substances in solution. Commercial SPE cartridges contain adsorbents which may be silica-based or polymeric, and recently molecularly imprinted polymers have become available as SPE adsorbents (see, for example, WO 01/55235 and WO 01/30586, the contents of which are incorporated herein by reference). The toxin is eluted from the adsorbent as a solution which is applied to the head of the mini-column so that the toxin is immobilised on the mini-column.

Mini-columns commercially available for the detection of aflatoxins typically are packed with layers of calcium sulphate, silica gel, alumina, Florisil™ and calcium sulphate, with cotton wool or paper pulp at each end to hold the layers in the column. Florisil is a hard, porous, granular substance, and is a brand of activated magnesium silicate typically used in vitamin analysis, chromatography, and antibiotic processing [see U.S. Pat. No. 2,393,625]. The columns may be glass or plastic tubes of 3-6 mm internal diameter, with a wider upper section for ease of addition of the sample. For example FIG. 1 of the accompanying drawings shows a minicolumn of borosilicate glass selected for minimal blue fluorescence under UV black light (365 nm), which is 5 mm outer diameter, 3.4 mm inner diameter and 12 cm long, fused to a 3 cm length of 14 mm outer diameter borosilicate glass to act as a reservoir.

International Patent Application WO 89/03037, the entire disclosure of which is incorporated herein by reference, discloses adsorbents having structure-selective affinities to various mycotoxins commonly occurring in agricultural commodities and foodstuffs. The selective adsorption properties of these materials enables the construction of a mini-column which can immobilize selected mycotoxins at certain physical locations in the mini-column thereby permitting the resolution and subsequent detection of mycotoxins extracted from samples of grain, oilseeds, and the like.

This immobilization phenomenon also enables separation of mycotoxin(s) of interest from interfering compounds. Interfering compound are most commonly other fluorescent species. However substances which quench the fluorescence of the analyte and/or interfere with the excitation of the analyte are also considered interfering compounds for the purposes of this disclosure.

In conventional mini-columns the affinities of the packing adsorbent are such that for all practical purposes no significant elution of the target compound from its selective adsorbent takes place when the recommended types and quantities of dissolving solvents and transporting or wash solvents are used and detection takes place with the mycotoxin within the test device.

The minerals and the mycotoxins which they selectively bind or otherwise immobilize include: Florisils for aflatoxins; bayerite for ochratoxin A, sterigmatocystin, and citrinin; pseudoboehmite for ochratoxin A, zearalenone, and citrinin; alumina for zearalenone, deoxynivalenol, patulin, sterigmatocystin and ergots; and, silica gel for patulin, sterigmatocystin and ergots.

For binding and immobilizing certain mycotoxins, the following minerals have been found to be effective: for ochratoxin A, pseudoboehmite and other aluminium oxides including bayerite, gibbsite, boehmite, bauxite and alumina (activity grade IV or V); for zearalenone, neutral alumina and other aluminium oxides (of activity grade I or II), including acidic or basic alumina, bayerite, bauxite, boehmite, pseudoboehmite, and gibbsite; for patulin, acidic alumina and other aluminium oxides including bayerite, gibbsite, boehmite, pseudoboehmite, and bauxite, and silica gel; for sterigmatocystin, neutral alumina (grade I), and other aluminium oxides including boehmite, pseudoboehmite, bauxite, gibbsite, and bayerite; for deoxynivalenol, neutral alumina and other aluminium oxides including bayerite, boehmite, pseudoboehmite, bauxite, gibbsite, and acidic alumina, and silica gel; for citrinin, bayerite, pseudoboehmite, bauxite, gibbsite, boehmite, and alumina; and, for ergots, alumina and silica gel. Bayerite, pseudoboehmite, and alumina are all forms of aluminium oxide (alumina).

A mini-column suitable for the measurement of aflatoxin B1 and total aflatoxins (aflatoxin B1, B2, G1 & G2) may contain, for example, the following adsorbents (beginning at the bottom of the column): plug e.g. Blue Tac™ (0.3 cm); dry sodium sulphate (1 cm); dry Florisil (1 cm); silica gel 60 (3 cm); dry sodium sulphate (3 cm). A similar alternative column has a layer of neutral alumina (1 cm) added between the silica gel and the dry sodium sulphate.

A mini-column for ochratoxin A may comprise (beginning at the bottom of the column): Blue Tac plug (0.3 cm); dry sodium sulphate (1 cm); acid washed sand (0.5 cm); pseudoboehmite (0.5 cm); dry sodium sulphate (2.0 cm).

The excitation unit is typically a light source or other UV source and an excitation filter, which restricts the light output of the light source to the wavelength that excites fluorescence in the immobilised mycotoxin or other moiety. The wavelength suitable for excitation of aflatoxin is about 365 nm and so the filter is adapted to transmit that wavelength or a band including that wavelength. Xenon lamps or light emitting diodes with a substantial UV content or UV-emitting diodes are suitable sources with an output including the desired wavelength.

The detection unit is typically a photodiode which is sensitive to the wavelength emitted by the fluorescing mycotoxin and an emission filter which is adapted to transmit that wavelength. Alternatively a photomultiplier may be used. The emission wavelength of immobilised aflatoxins is typically within the range 400-450 nm, depending upon the combination of solvent and adsorbent.

After development of the layer or band of mycotoxin in the minicolumn, it is removably mounted in a holder in the device, typically in an upright position, in a position where it is in the path of radiation emitted from the excitation unit. The detection unit is positioned in the housing so as to be in the path of fluorescent emissions from the band of mycotoxin, or other moieties, in the minicolumn. The components of this system: UV source (here a Xenon flash lamp), excitation filter, minicolumn, emission filter, detector (here a photodiode), and including a reflector positioned behind the lamp, are shown in FIG. 2 of the accompanying drawings. A preferred arrangement uses two detector units as shown in FIG. 3 of the accompanying drawings. The detector units are placed on either side of the light path from excitation filter to the minicolumn. In this way, fluorescence is detected from substantially 180° of the external surface of the minicolumn, increasing the accuracy of the measurement of the amount of light emitted from the sample. An absorbing surface behind the minicolumn prevents back reflections that might interfere with the emission detector.

Most suitably the minicolumn is mounted in a holder that is rotatable through 180° so that emission can be detected from substantially 360° around the sample. The holder may be manually rotatable as shown in FIG. 4 of the accompanying drawings. Alternatively the holder may be motorised to rotate through 360°, either using the dual detector system shown in FIG. 4 or a single detector that scans a narrower portion of the surface of the minicolumn. A further option is the use of multiple detectors positioned around a non-rotatable minicolumn. However the ability to capture emission from a 360° angle to measure the total emission is an important aspect of the invention, because the mycotoxin and the fluorescence may be unevenly distributed in the immobilised band.

The holder shown in FIG. 4 has a sleeve portion that covers the layers of the minicolumn except for an aperture at the point where the mycotoxin is immobilised by the selective adsorbent. In this way the risk of false emissions or reflections from irrelevant parts of the minicolumns is avoided.

As mentioned above, a minicolumn may be provided with multiple adsorbent layers to immobilise more than one mycotoxin in a sample. In such a case, the holder may be provided with a screw drive so that the minicolumn is raised or lowered in the holder relative to the light path of the excitation, so that the respective bands are exposed through the aperture shown in FIG. 4.

The signal from the photodiodes generated by the emitted fluorescent radiation is fed into a processing unit as shown in FIGS. 5 and 6 of the accompanying drawings allowing calculated values relevant to the amount of mycotoxin in the sample to be displayed on an alpha-numeric display device. Using samples with standardised quantities of toxin, it has been shown that a plot of the intensity of the fluorescence against quantity of toxin is substantially linear. Accordingly the processor unit can be calibrated with two or more standard samples, or other suitable fluorescent compounds, to generate internal reference coordinates by which the intensity of an unknown sample can be allocated a numerical value of the amount of toxin in the sample.

Figure 7:
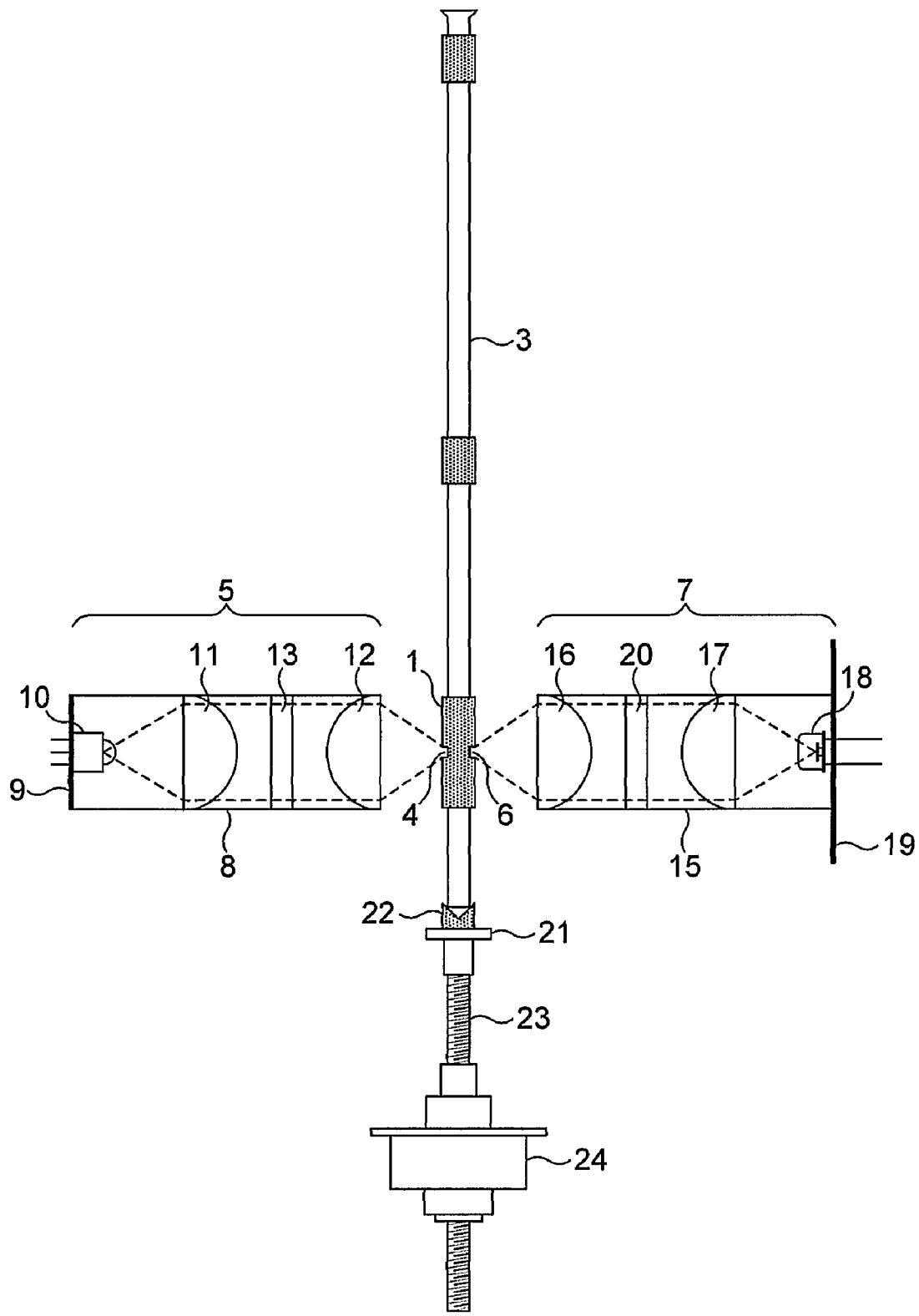
FIG. 7 is a schematic side view of the principal components of another embodiment of a device.
Figure 8:
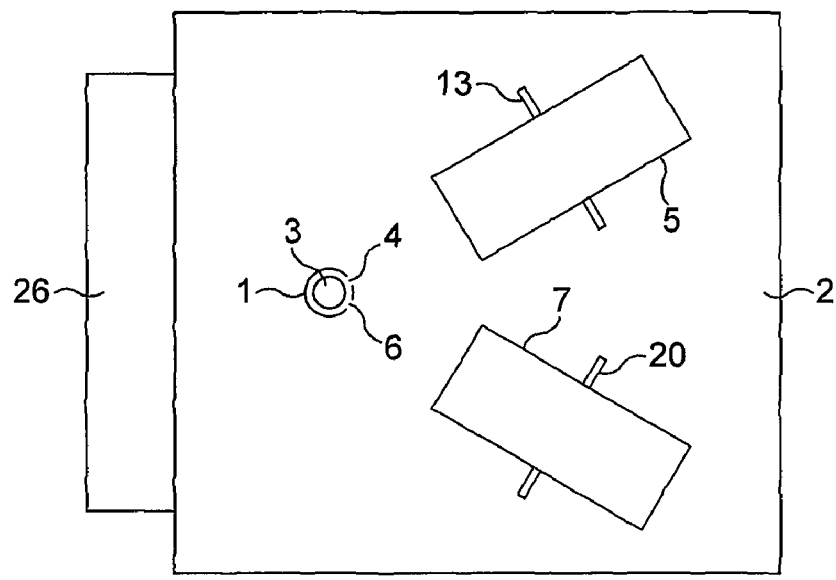
FIG. 8 is an over-head view of the excitation/detection arrangement of the embodiment of FIG. 7 as configured for use.
Figure 9:
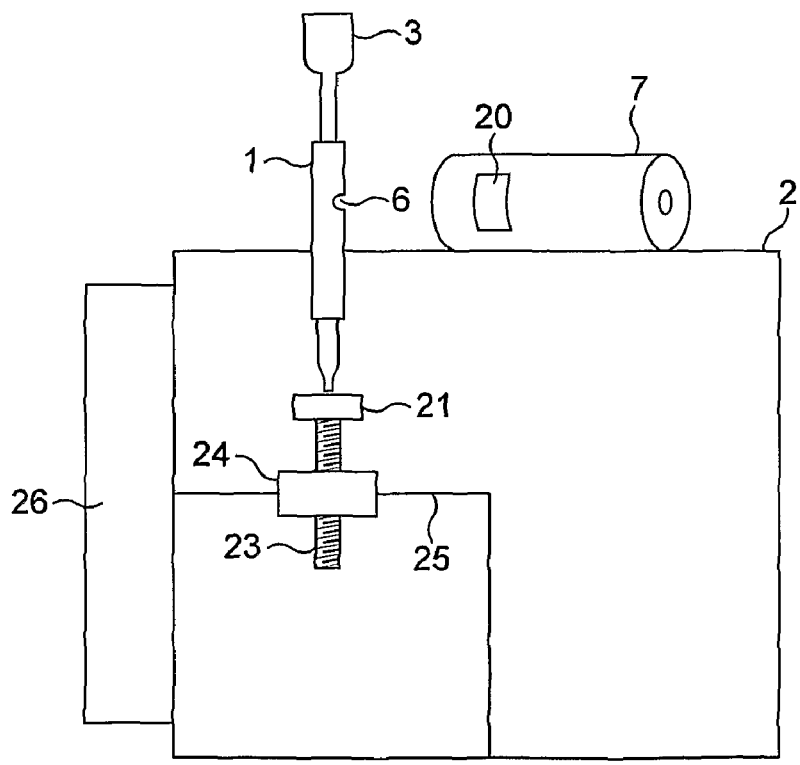
FIG. 9 is a side view of the arrangement of FIG. 8.

In another embodiment of the device, shown in FIGS. 7-9, the sample holder is fixed relative to it's mounting, and the sample-containing column is movable within the holder to allow a 360° assessment of the fluorescence.

The key elements of this embodiment of the device are shown in FIG. 7. A tubular holder 1 is mounted on a support platform 2 (not shown in FIG. 7) to receive a mini-column 3. The mini-column 3 contains an adsorbent packing in which a toxin can be immobilised as a layer or band as described earlier. The holder has a first side aperture 4 to allow excitation energy form the excitation unit 5 to impinge on the layer of toxin through the glass wall of the mini-column and excite fluorescence of the immobilised toxin, or other moiety. A second side aperture 6, at 90° to but in the same horizontal plane as aperture 4, allows fluorescence emitted from the toxin layer to be captured by the detection unit 7. The mini-column is positioned within the holder 1 so that the immobilised layer of toxin is in, or overlaps, the same plane as the apertures 4,6.

The excitation unit 5 comprises an optical tube mount 8, with light-absorbing interior surfaces, aligned with the aperture 4. The end of the optical mount 8 remote from the holder 1 is closed by a circuit board 9 with electrical connections for a light (preferably UV) emitting diode mounted on the board 9 within the tube 8. Within the tube 8 a collimating lens 11 collimates the radiation emitted by the diode 10, and the collimated radiation is brought to a focus within the holder 1 via the aperture 4 by a lens 12 at the other end of the tube 8. Interposed between the lenses 11,12 is an interference filter 13 which passes radiation with a band of energy suitable to excite fluorescence in the intended target. Suitably the filter 13 is slidable within slots in the tube 8 so that it can be replaced easily or changed to provide a different characteristic wavelength band for excitation.

The detection unit 7 comprises an optical tube mount 15, with light-absorbing interior surfaces, aligned with the aperture 6 in the holder 1. The end of the optical mount 15 adjacent the holder 1 contains a collimating lens 16 which collimates the radiation emitted by the fluorescing toxin in the aperture, and the collimated radiation is brought to a focus by a lens 17 at the other end of the tube 15. The emitted radiation is focussed on a photodiode 18 mounted on a circuit board 19 with appropriate electrical connections to hand on the signal from the photodiode. Interposed between the lenses 16,17 is an interference filter 20 which passes radiation known to be associated with fluorescence of the intended target. Suitably the filter 20 is slidable within slots in the tube 15 so that it can be replaced easily or changed to provide a different characteristic wavelength band for excitation. More preferably a set of different filters is mounted on a wheel for rotation through the tube, for use in the situation where multiple toxins are adsorbed in different layers in the mini-column. In the schematic view of FIG. 7, for convenience the apertures 4,6 and the excitation and detection units 5,7 are shown in a direct line with each other. In practice, the tubes 8,15 are placed at an angle to each other to minimise any risk of stray radiation from the excitation unit entering the detection unit, and to optimise the footprint of the system. FIG. 8 shows a convenient 90° arrangement.

When the mini-column 3 is placed into the holder 1, its lower end locates against a support plate 21. Because the position of the immobilised toxin layer in the mini-column may vary between different columns, the plate 21 is preferably adjustable vertically up and down so that the toxin layer can be brought into the plane of the apertures 4,6. Additionally, vertical movement allows the system to be used to investigate multiple bands in which different toxins are immobilised on stacked layers of adsorbents.

The fluorescence emanating from the emission aperture arises from the small part of the toxin layer that is exposed at the excitation aperture. The light is then transmitted through the cartridge/mini-column and the fluorescent radiation exits via the emission aperture(s) to the detector. By arranging for the mini-column to be rotatable and moveable vertically relative to the excitation and emission apertures means that the small part of the toxin layer that receives the excitation radiation and is viewed changes during rotation and vertical movement (i.e. the small part of the toxin layer viewed is scanned across the surface of the toxin layer) so that readings can be taken from the whole of the toxin layer as it is exposed in the excitation aperture 4. Suitably the end of the mini-column is firmly located in a gripping socket 22 mounted on the support plate 21, so that rotation of the support plate 21 also rotates the mini-column 3.

In the device shown in FIGS. 7-9, the two motions are conveniently combined as the support plate 21 is mounted on a screw-threaded rod 23 which is driven by an actuator motor 24 in the form of a digital linear actuator. Accordingly, rotation of the rod 23 both rotates the support plate 21 and moves it vertically. It is important that the pitch of the thread of the rod 23 is restricted to a value at which rotation of the mini-column through 360° does not move the toxin layer beyond the window of the apertures 4,6.

As seen from FIGS. 8 and 9, the device is given a unitary nature by providing a support staging, and mounting the holder 1 and excitation and detection units 5,7 on an upper platform 2 and the motor 24 on a lower platform 25. The staging also supports a processor unit 26 in which a microprocessor is used to control power supply to the motor 24 and LED 10 (FIG. 7) and to process the signal output from the photodiode 18 (FIG. 7). For laboratory use, the processor unit may be connected to mains electricity for power. However the use of LEDs and photodiodes of low power consumption means that the device can easily be used with battery power for field use.

The signal from the photodiode 18 may be processed onboard to give a direct read-out as in FIGS. 5 and 6, or may be fed to a computer. On the computer the data from the microprocessor can be used to give a real-time graphical displays of intensity against time and against rotational and/or vertical position of the support table 21 and hence the mini-column 3.

In practice, because of the variable position of the immobilised band of toxin in the minicolumn, the support plate 21 is typically set at it lowest position when a minicolumn is placed into the holder 1 and engaged with the gripper 22. The motor 24 is then actuated to move the minicolumn upwardly while the detection unit observes the fluorescence emanating from the aperture 6. The systems then 'hunts' for the location of the region or regions of higher intensity, which will reveal the presence of fluorescing band(s) of toxin(s). In the region of higher intensity, many intensity readings are recorded during each 360° rotation of the minicolumn. Intensity readings are recorded during 360° rotations of the minicolumn at several positions (heights) within the region of high intensity. The readings are summed to give a single value which can be compared with values previously recorded for standards to calculate a value of the amount of toxin in the original material from with the sample has been obtained.

In practice, a 'coarse' scan is undertaken initially in order to locate the fluorescent band. A 'fine' scan, involving smaller vertical steps, is then performed in order to measure the target compound. The region encompassed by the fine scan can be defined. i.e. the scan can begin and end with different degrees of overlap between the excitation beam and the immobilised band. The maximum intensity will occur when the entire beam overlaps the immobilised band.

While the device has been described with reference to use of traditional minicolumns, it will be appreciated that the device can be used with other detection systems or 'cartridges' where the mycotoxin is immobilised in a band or layer from which fluorescence can be measured.

In one such arrangement, the 'traditional' mineral adsorbents in the minicolumns may be replaced by cartridges of SPE adsorbents described above, and especially by polymers that have been designed to recognise and immobilise mycotoxins and other target compounds. Polymers may be in the form of non-imprinted ('blank') polymers or molecularly imprinted polymers (MIPs). Blank polymers are designed using computer simulation methods whereas molecular imprinting is achieved by co-polymerising functional and cross-linking monomers in the presence of the target molecule, which acts as a molecular template. In the latter case, the functional monomers arrange specifically around the molecular template, and are subsequently held in position by polymerisation with a usually high degree of cross-linking. After polymerisation the molecular template is extracted from the polymer, revealing complementary binding sites that allow rebinding of the target molecule with in many cases very high specificity, comparable to that of antibodies. Imprinted polymers can be used in organic solvents, and because of their great chemical, thermal and mechanical stability, they retain their molecular memory over long time periods and in harsh environments.

In the case of blank polymers, a combination of monomers is selected that produce a polymer which is sufficiently specific to the compound of interest without the need for an imprinting step.

When a solution of target compound is applied to a cartridge or cuvette packed with a MIP or selective 'blank' polymer, the isolation of the compound as a layer in the packing is closer to a chromatographic separation than the immobilisation achieved by the adsorbent in a conventional mini-column. However the selectivity means that the target compound forms a band that moves only slowly through the packing and is not eluted from the column. Accordingly the column may be inserted in the holder of Apparatus with a band of the target compound which can be assessed for fluorescence in the same way as the immobilised layer in a traditional mini-column.

In another system of 'cartridge' that may be used in the device the adsorbent is provided as a coating on the surface of a glass or plastic rod. Additional arrangements involve the application of the adsorbent onto the inner surface of a column or onto the inner surface of a cuvette (see for example then system used by Piletsky et al in Biosensors and Bioelectronics, Volume 16, Issues 9-12, December 2001, pp 701-707).

As mentioned above, a polymer adsorbent may be used to trap the toxin in a 'clean-up' step. This may provide an opportunity for the 'clean-up' step to be eliminated since the toxin trapped as a band in the polymer adsorbents may be placed directly in the device. However, when necessary or desired a polymer column, or similar SPE column, may be used for clean-up purposes followed by a separate immobilisation step.

A suitable clean-up protocol is as follows:

This method has been developed from known HPTLC and HPLC methods that employed a clean-up step using phenyl-bonded solid phase extraction (SPE). The existing methods were applicable to a wide range of cereal and oilseed matrixes, and most animal feeds, including those containing citrus pulp. To adapt the method for quantification by using Apparatus in accordance with this invention, it was necessary to produce a faster procedure and to increase the weight of sample in the final extract to allow sufficient aflatoxin to be trapped on a solid phase.

The faster procedure was achieved by reducing the volumes of diluted extract that needed to be passed through the SPE column from 70 ml down to as little as 8 ml, although more typically 16 ml. This reduced the time for this clean-up from ca 20 minutes down to ca 5 minutes.

The increased weight of sample in the final extract was achieved by reducing the meal to solvent ratio to as low as 1:2 and reducing the volume of eluent from 7 ml to as little as 2 ml.

A crude methanol/water extract is cleaned-up using a reverse phase SPE column, such as phenyl-bonded (Varian) or Strata X (Phenomenex), each incorporating an integral zinc acetate clean-up. Aflatoxin is eluted from the SPE column with 2 ml of dichloromethane which is passed through anhydrous sodium sulphate prior to addition to a normal phase minicolumn.

Alternatively, the crude methanol/water extract may be cleaned-up and immobilised directly onto blank polymers, molecular imprinted polymers (MIPs) or virtual imprinted polymers (VIPs).

1. Scope

This method should be applicable to a wide range of edible nuts, cereals, oilseeds and other food matrixes, and most animal feeds, including those containing citrus pulp. It is designed to work to EU regulatory limits.

2. Principle

A methanol:water (4:1) extract of the maize sample is diluted with 1% acetic acid and a zinc acetate precipitation is carried out. The partially purified extract is then applied directly to a solvated, phenyl-bonded or Strata X solid phase extraction (SPE) column that retains the aflatoxin and lets the more polar impurities pass. The column is then washed with water and dried by air-flow. The aflatoxins are eluted from the column using dichloromethane and the eluent is dried by passing it through a column containing granular, anhydrous sodium sulphate. The purified extract is applied directly into a mini-column.

The SPE clean-up can either be performed in batches of 10 or 12 using a vacuum manifold, or if this is unavailable, then single columns can be run using either a Buckner flask vacuum system, or a syringe over-pressure system.

Alternatively, a small portion (e.g. 4 ml) of the 80:20, water:methanol extract of the maize sample is applied to a cartridge containing polymeric material that is tailored to specifically recognise the target compound. The cartridge is then washed with a small quantity (e.g. 1 ml) of 80:20, water:methanol in order to remove interfering compounds from the immobilised target 3. Reagents Analytical grade reagents should be used, unless otherwise stated, and distilled water should be used to prepare all aqueous reagents.

3.1 Methanol, technical or general purpose reagent (GPR)

3.2 Extraction solvent, methanol-water (80:20). Add 200 ml water to 800 ml methanol and mix well.

3.3 Zinc acetate dihydrate. Dissolve by warming a solution of 200 g zinc acetate dihydrate in 900 ml water. Add 3 ml glacial acetic acid and make up to a 1 litre mark.

3.4 Acetic acid solution (1%). Add 10 ml glacial acetic acid to 990 ml water 3.5 Celite, Hyflo Super Cel (e.g. NBS Biological), or use methanol washed Celite 545. Add enough methanol to Celite 545 (Manville (GB)) to prepare a slurry, and then filter under vacuum using a Buckner funnel, sucking as dry as possible.

3.6 Sodium sulphate, anhydrous, crystalline/granular. Dry in oven at 105° C. for 2 hours and store in a desiccator over silica gel.

3.7 Dichloromethane, AR 3.8 Dichloromethane-acetone development solvent (9:1). Add 10 ml acetone to 90 ml dichloromethane in a 100 ml Quickfit conical flask fitted with a stopper. Add about 10 g of dried sodium sulphate. After use, allow to evaporate to dryness in an open beaker in a fume cupboard, do not add mixture to bulked organic waste because there is a risk of explosion under basic conditions.

3.9 Column packing materials: silica gel 60, 63-200 μm; florisil, 100-200 μm both dried at 105° C. for 2 hours 3.10 Aflatoxin Standards. Dissolve thin films of aflatoxins $B_1$, $B_2$, $G_1$, and $G_2$ in toluene acetonitrile (see 3.8), to give UV solutions at approximately 10 μg/ml. Determine the concentration of the UV solutions by spectrophotometry, see AOAC Natural Toxins, Chapter 49, 970.44, but with molar absorptivities ($\epsilon$) modified for substitution of benzene by toluene. To calculate the concentration (c), substitute in the equation:

$$c(\mu g\ aflatoxin/ml) = A \times MW \times 1000/(\epsilon)$$

where A = the maximum UV absorbance in the region of 350 nm
MW = Molecular weight
($\epsilon$) = molar absorptivity

TABLE 1

Molecular weight and molar absorptivity of the aflatoxins in toluene-acetonitrile 98:2)

| Aflatoxin | Molecular Weight (MW) | Molar Absorptivity ($\epsilon$) |
|---|---|---|
| $B_1$ | 312 | 19,300 |
| $B_2$ | 314 | 20,400 |
| $G_1$ | 328 | 16,600 |
| $G_2$ | 330 | 17,900 |

4. Apparatus 4.1 Acid Washed Glassware. Aflatoxin can be bound strongly to basic sites on glassware, particularly if the items are new, have been soaked in bleach, or have been washed in a basic detergent. To avoid these losses, soak glassware for 2 hours in 4 M sulphuric acid and then rinse very thoroughly with distilled water until the pH of the rinse water is neutral. Note, losses can be higher in acid washed glassware that has been inadequately rinsed, than in none acid washed glassware. Potential losses are highest in glassware used to take solutions containing aflatoxin to dryness.

4.2 Flask shaker for 500 ml Erlenmeyers, wrist action or reciprocating (not orbital)

4.3 High speed blender, explosion proof, 1 litre jar, optional 4.4 Laboratory balance, to weigh samples at 50 g+/−0.1 g.

4.5 Laboratory oven, ventilated or forced air, to give 105° C.+/−5° C.

4.6 Erlenmeyer flasks, glass stoppers, 500 ml and 250 ml.

4.7 Measuring cylinders, 250 ml, 10 ml.

4.8 Filter papers, medium or medium fast, e.g. Whatman No. 1, 24 cm or Whatman 2V. Also medium or medium fast filter paper, 15 cm if syringe option (4.10c) is used.

4.9 Solid phase extraction (SPE) columns, phenyl-bonded, 500 mg, 3 ml column (e.g. BondElut by Varian) or Strata X (Phenomenex)

4.10 System to run SPE columns:

a) Sample processing station, preferred, vacuum manifold with 10 or more ports (e.g. Vac-Elut system by Varian and VacMaster by IST International). Vacuum line fitted with a trap needed e.g. diaphragm pump, or water aspirator pump to give 15 to 20 inches of mercury (−50 to −70 kPa).

or b) Single column vacuum system. Fit a female luer needle to an SPE column (4.8). Push the needle through a bored rubber bung and fit the bung into a filtration flask connected to a vacuum line.

or c) Single column syringe system. Fit a 70 ml syringe containing a frit (20 μm polyethylene) onto an SPE column using a luer adapter and force liquid through the column by gently pressing the plunger.

4.11 Reservoirs, 70 ml, fitted with a 20 μm polyethylene frit, male luer.

4.12 Reservoirs, 15 ml, male luer.

4.13 Empty 3 ml SPE columns, fitted with a 20 μm polyethylene frit (used SPE columns can be emptied)

4.14 Sodium sulphate columns. Using a small funnel, two-thirds fill a 3 ml SPE column (4.13). Store in a desiccator.

4.15 Adapters to connect SPE columns to reservoirs.

4.16 Glass vials, 7 ml with foil-lined caps 4.17 Glass vials, 1.5 ml, amber, complete with septa caps and septa 4.18 Sample concentrator or other means to evaporate solvent from vials at <=45° C. and preferably under a stream of nitrogen.

4.19 UV lamp, long-wave 366 nm, 6 or 8 watt, preferably in a viewing cabinet.

4.20 Volumetric flasks and stoppers, 5 ml Grade A, amber.

4.21 Microlitre syringes, calibrated, direct displacement, 25 to 500 μl.

4.22 Vortex mixer 4.23 UV spectrophotometer for determining the concentration of aflatoxin standards.

4.24 Minicolumns, borosilicate glass selected for minimal blue fluorescence under UV black light (365 nm), 5 mm od, 3.4 mm id. 12 cm long fused to a 3 cm length of 14 mm od borosilicate glass to act as a reservoir.

4.25 Column packing: plug end of column with cotton wool; add dry sodium sulphate to give 1 cm base; add 1 cm dry florisil; add 3 cm silca gel 60; add 3 cm dry sodium sulphate. Tamp to compress each adsorbent and ensure a flat, horizontal interface between florisil and silica gel.

4.26 Means for relatively moving the sample cartridge and the detection unit whereby the radiation may be sensed in the form of a dual motion actuator (for example as supplied by Haydon Switch and Instrument Inc. under the title Series LR 3500 Dual Motion Sensor.

5. Procedures

The work should be carried out in efficient fume cupboards to protect the analyst from potentially toxic dusts and solvents. Appropriate gloves should be worn to prevent skin adsorption of toxins. In solution, the aflatoxins are unstable when subjected to UV light, so direct sun-light should be screened out, and tungsten rather than fluorescent lighting must be used.

5.1 Extraction

Weigh 50 g+/−0.1 g of maize meal into a 500 ml Erlenmeyer flask and add 100 ml methanol-water (80:20) extraction solvent (3.2). Stopper the flask and shake vigorously (4.2) for 45 minutes. Alternatively blend at high speed (4.3) for 3 minutes. Filter (4.8) under gravity into a 250 ml Erlenmeyer flask.

5.2 Clean-Up

Using either a SPE sample processing station (4.10a) or single column vacuum system (4.10b), or a syringe over-pressure system (4.10c), the zinc acetate clean-up is integrated into the SPE clean-up, as described below. See Diagram 4 for an outline of the configuration of columns and reservoirs at each step.

5.2.1 Fit the required number of SPE columns (4.9) into the vacuum manifold and close the column taps, or place a single column into a Buckner flask, and label the columns as appropriate.

5.2.2 SPE column solvation: measure 5 ml of methanol (3.1) into a measuring cylinder and add 2 ml of this to the column. Using an adapter (4.15), connect a 70 ml reservoir to the column and add the remaining 3 ml of methanol. Open the taps on the vacuum manifold and apply a slight vacuum to pull the methanol through the column. Turn the taps off when the reservoir is empty, leaving a head of about 2 cm of methanol above the column packing. Add 10 ml of water to the reservoir, open the taps and apply a vacuum to give a flow rate of 3 to 5 ml per minute. Close the taps when the reservoir is empty, again leaving a head of liquid in the column. If a column should run dry, repeat the salvation procedure.

Columns can be solvated and then sealed with plugs for later use 5.2.3 Loading the reservoir/zinc acetate precipitation: Sequentially add the following; 0.5 g scoop of celite (3.5), 10 ml of 1% acetic acid (3.4), 4 ml of sample filtrate (5.1), and 2 ml of zinc acetate solution (3.3) to precipitate out unwanted compounds. Open the column taps and set the vacuum for a flow of 3 to 5 ml/minute. DO NOT let the columns run dry.

5.2.4 Washing the SPE column: As soon as the reservoir is empty, switch off the tap to keep a head of liquid on the column. Usually all columns are brought to this stage and 10 ml of water is added to each of the reservoirs. The taps are then opened and the vacuum is adjusted to give a flow of about 5 ml/minute.

5.2.5 Drying the SPE column: Let the column(s) run to dryness, and then apply full vacuum available for 3 minutes to draw through the maximum volume of air to remove as much water as possible. Release the vacuum and remove the SPE columns. Use a tissue to dry any remaining droplets of water inside the column and an airline can also be used to blow down the column if required.

5.2.6 Elution of aflatoxin: Connect a sodium sulphate column (4.14) to the bottom of the SPE column using an adapter (4.15). Dispense 2 ml of dichloromethane (3.7) into the SPE column and then fit a 20 ml plastic syringe onto the SPE column to apply gentle over-pressure. Add the eluent directly onto a packed minicolumn (4.25)

5.2.7 Alternative syringe system clean-up: Using the syringe set-up (4.10c), sequentially add: 0.5 g scoop of celite (3.5), 10 ml of 1% acetic acid (3.4), 4 ml of sample filtrate (5.1), and 2 ml of zinc acetate solution (3.3) to the syringe. Gently press the plunger to force this solution through a solvated SPE column at a flow rate of 3 to 5 ml per minute, again taking care not to let the column run dry. Load the syringe with 10 ml water, and use this to wash the SPE column. Dry the SPE column thoroughly by passing compressed air through it, and then fit a sodium sulphate column (4.14) onto the luer fitting of the SPE column. Using a 20 ml syringe, pass 2 ml of dichloromethane very slowly through the SPE and sodium sulphate columns and add the eluent directly onto a packed minicolumn (4.25)

5.3 Mincolum Clean-Up/Toxin Immobilisation (This Step Should be Performed in a Fume Hood)

5.3.1 A packed minicolumn (4.25) is held vertically, preferably using a rack, and the dichloromethane eluent (~2 ml) is applied directly into the reservoir of the minicolumn. The minicolumn can be allowed to run under gravity, or a slight over-pressure can be applied using a pipette filler 5.3.2 Just as the meniscus reaches the top of the sodium sulphate top layer, 2 ml of dichloromethane/acetone (3.8) is added, and again this can pass under gravity or slight over-pressure. Flow may be slowed if ice builds up at the bung. To prevent this, a filter paper or tissue can be touched against the bottom of the column to diffuse away the solvent, minimising evaporation at the bung.

5.3.3 The minicolumns can be observed under a UV viewing cabinet (4.19) to check that tight blue aflatoxin bands have been produced at the Florisil/silica gel interface.

5.4 Quantification 5.4.1 Calibrate an instrument as described in FIGS. 7-9 using ‘high’ and ‘low’ standards 5.4.2 Place a sample minicolumn in the holder of the device and operate to obtain the aflatoxin reading directly in μg/kg.

We now refer to FIGS. 10, 11 and 12 which show a further embodiment of the invention.

The apparatus of the invention is contained within a generally rectangular housing 101. Within the housing is mounted a chassis. The top of the chassis mounts a mounting means 102 for mounting a sample cartridge which in FIGS. 11 and 12 is in the form of a mini-column 104. The mount 102 may be adapted so as to mount other types of sample holding cartridges or containers.

The rectangular housing 101 has a suitable aperture on the top surface thereof through which the mini-column 104 may be inserted into the mounting means 102.

Referring now to FIG. 11, an optical module 105 comprises components 106-114. An ultra-violet LED 106 is provided as a source of suitable radiation. The beam of radiation from the source 106 passes through a collimating lens 107 to provide a collimated beam, then through a band limiting filter 108, the wavelength of the band of which is chosen so as to excite fluorescence in the sample, to a focusing lens 109. The focussed beam is then directed through an excitation aperture 4 at the sample in the mini-column 104. Fluorescence produced is collected through a collection aperture 6 by a collimating lens 111, and passes through a band selection filter 112 and a collimating lens 113 to a detector 114 in the form of a photodiode mounted on a screening box 115. The apertures 4 and 6 define the particular area of the target which is being examined at any one time.

Figure 12:
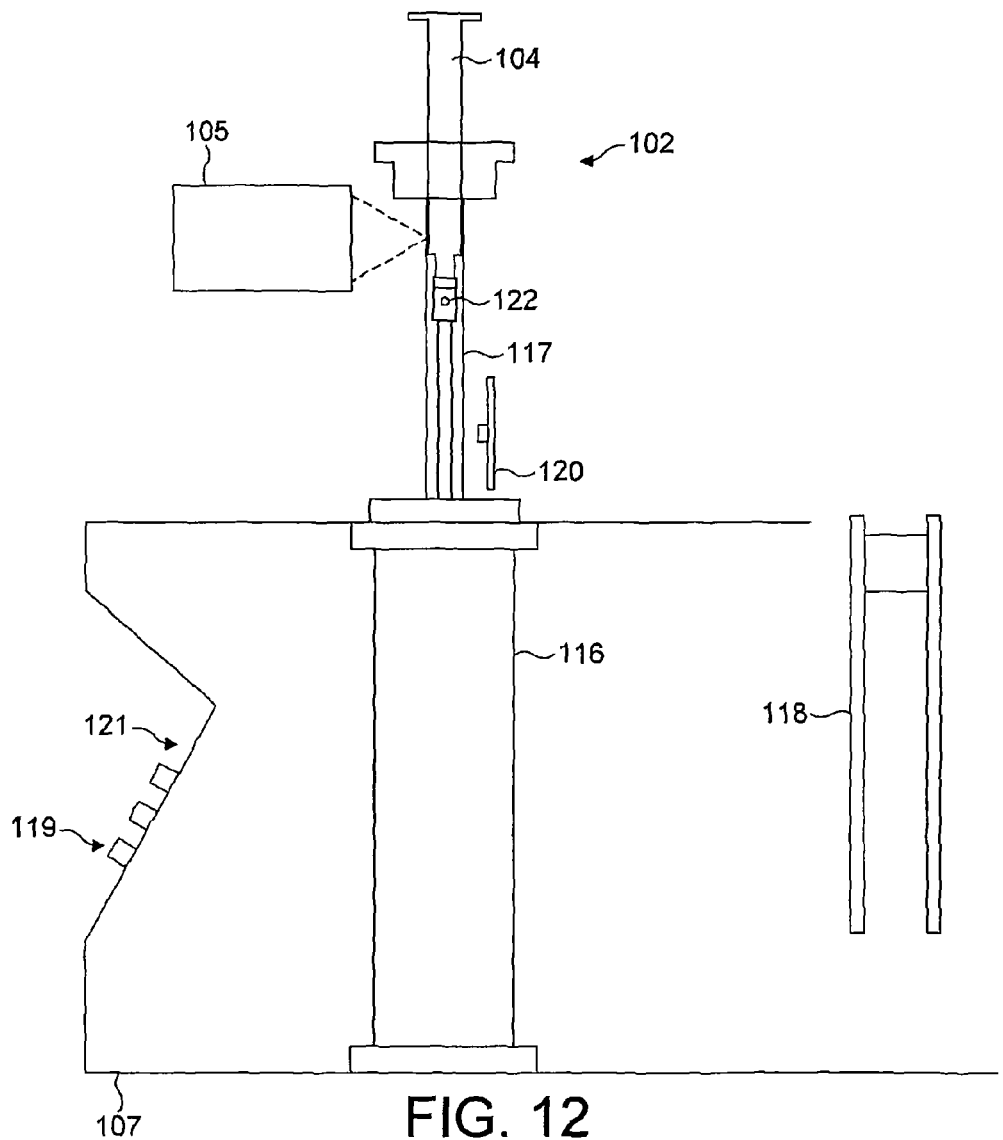
FIG. 12 is a side view, partly in section, of the embodiment of FIG. 11.

Referring now to FIG. 12, it will be seen that within the lower part of the rectangular housing 101 and mounted on the chassis is a dual motion actuator 116. This comprises two electric stepper motors, one of which (stepper motor A) is arranged to linearly or axially move a shaft 117 on which is mounted the mounting means 102, and the other of which (stepper motor B) is arranged to rotate the shaft or cartridge support tube 117. The cartridge support tube 117 mounts the mounting means 102 which in turn mounts the mini-column 104 and so as the cartridge support tube is rotated and moved axially (linearly) by the stepper motors A and B, the mini-column 104 is similarly rotated and moved linearly with respect to the optical module 105. The cartridge support tube 117 also mounts a position magnet 122 which is mounted in such a position that as the cartridge support tube moves, the position magnet 122 passes a Hall effect position sensor 120.

As will be understood, the stepper motors are arranged so as to rotate or axially move the cartridge support tube 117 in steps (which may be merged so as to rotate or move the cartridge support tube smoothly).

The stepper motors 106 are controlled by electronic components mounted on one or more printed circuit board 118. The manual input is provided by buttons or switches 119 mounted on the front face of the rectangular housing 106, and the information output may be via a suitable electronic coupling 123. A display 121 is also mounted on the front face of the rectangular housing 101.

Figure 11:
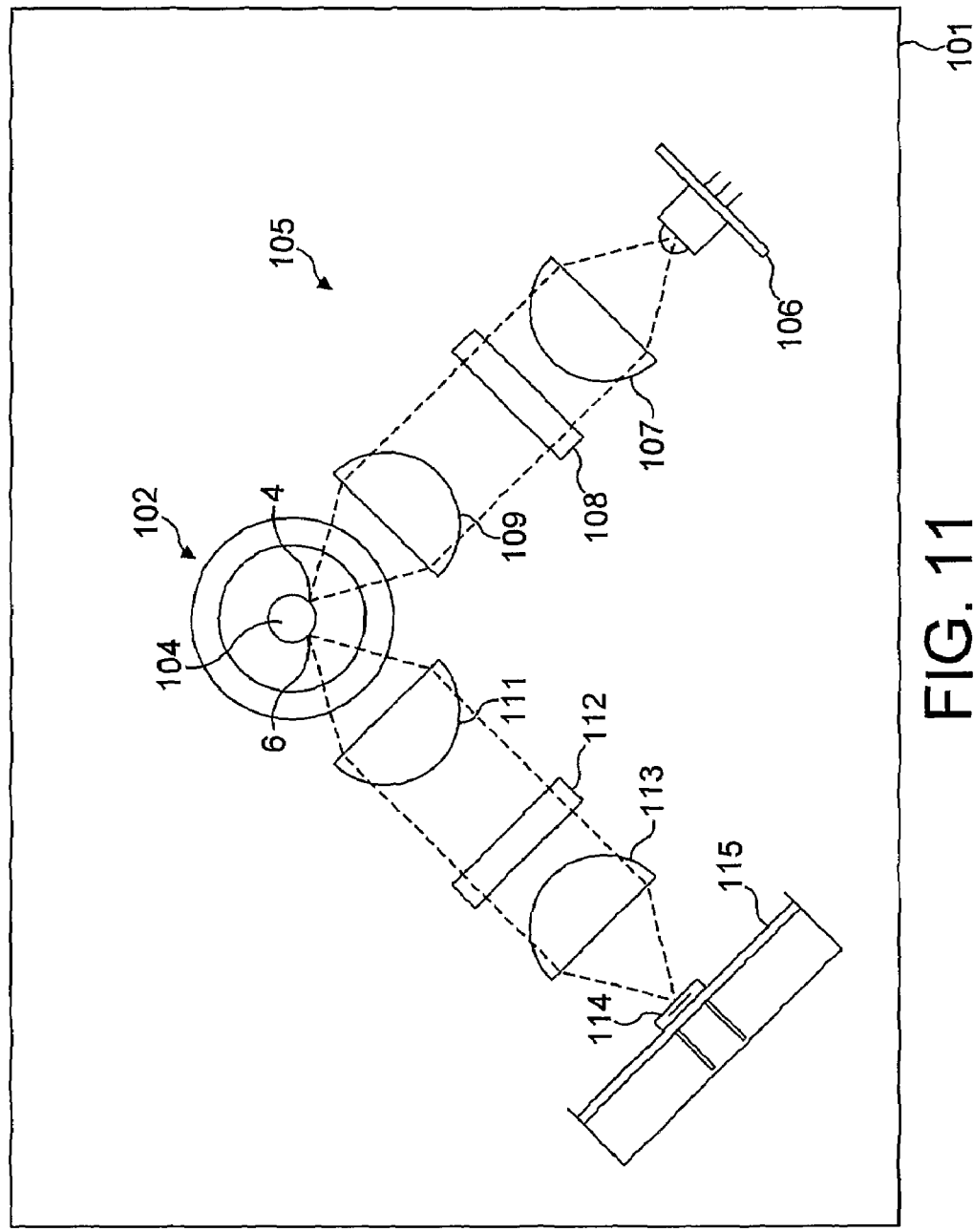
FIG. 11 is a plan view, partly in section of another embodiment of the invention.

The components described with respect to FIGS. 11 and 12 are mounted on the chassis.

Figure 10:
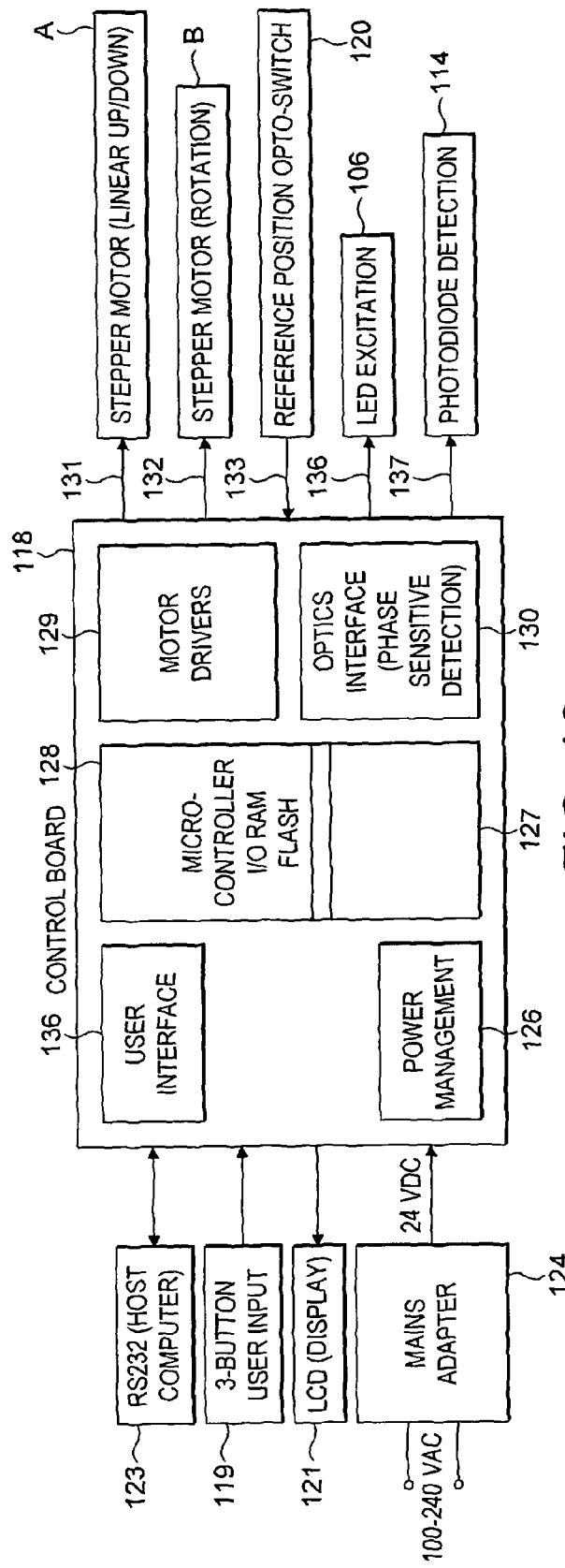
FIG. 10 is general arrangement of the electronic components of the device.

We now refer to FIG. 10 that shows a general arrangement of the components which are mounted on the PCB 118.

Power is provided to the apparatus via a mains adaptor 124 and is provided to a power management module 126 on the board 118. The program and operating system to run the apparatus of FIGS. 11 and 12 is contained within a microcontroller 128 attached to a field programmable gate array 127.

The optical components, and, in particular, the LED 106 and the photodiode detector 114 are controlled by an optics interface module 130 via lines 136 and 137 respectively and the output of the photodetector 114 is passed via line 137 to the optics interface module 130. In addition, there are provided a motor driver module 129 which includes 3 input/outputs, a first output 131 to the stepper motor A which provides a linear or axially up and down movement of the mounting means 102, a second output 132 to the stepper motor B which provides the rotation of the mounting means 102, and an input 133 which receives a signal from the Hall effect position switch 120 which provides an indication of the exact position (axially and rotationally) of the mounting means 102.

A user interface module 136 is provided to send and receive signals via the link to a host computer 123, and to the buttons 119, and to the display 121.

The actuator 116 comprising the two stepper motors A and B may conveniently be provided by a HSI Hybrid Dual Motion Motor provided by the Haydon Switch Instrument, Inc.

The arrangement may be such that 200 steps of stepper motor B provide a single revolution of the shaft 117 (so each step equals 1.8°) and the linear movement may be 20 micron per step of the stepper motor A. This enables the target to be scanned in a very fine manner.

The source 106 may be provided by, for example, a continuously or intermittently driven xenon lamp or a continuously or intermittently driven light emitting diode.

One or other of the band limiting filters 108, 112 may comprise a plurality of radiation filters which allow different wavelengths to pass and there is provided means to relatively move the radiation filters so as to bring each filter individually into the optical path between the radiation source 106 and the photodiode 114. The detection of different wavelengths allows one inter alia to analyse different toxins readily.

The plurality of radiation filters may be filter components of a filter wheel in which the filter components are individually brought into the optical path between the radiation source 106 and the photodiode 114 on rotation of the wheel.

Alternatively, the plurality of radiation filters may be provided by different areas of a continuous radiation filter.

The plurality of radiation filter wavelengths may be provided by a monochromator.

The apparatus of FIGS. 10 to 12 may be used in a similar manner to that described with respect to the earlier described embodiment.

In essence, a target in the form of a target compound, a derivatised target compound, or target compound-stimulated moeity, is collected in the sample cartridge in the form of a mini-column 104.

As a first, calibration step, a known quantity of the target, for example the toxin, comprising the toxin itself, a derivatised compound of the target or a compound-stimulated moiety of the toxin material under investigation is used to provide the target compound.

The cartridge is mounted in the apparatus of FIGS. 11 and 12 (in FIG. 11, the cartridge is in its uppermost position) and the stepper motors A and B are operated by pulses provided by the motor driver module 129. In a typical arrangement, the stepper motor A is initially driven rapidly so as to move the cartridge 104 rapidly from its lowermost to its uppermost position so that the position magnet passes the position sensor 120 and the part of the cartridge containing the target passes the apertures 4 and 6 and the optical module 105. In this way the vertical position of relevant fluorescence is detected by the detector 114. The first stepper motor A is then operated to move the cartridge to a predetermined position with respect to the detected fluorescent band (typically a position in which the start of the band half overlaps the excitation aperture 4). The stepper motor B may then be rotated relatively slowly through 360°, the stepper motor A translated by a single step, and then the stepper motor B rotated through 360° again. This process may be repeated until the extent of the target has been detected by detecting the fluorescent radiation.

The output signal indicative of the fluorescence detected by the photodetector 114 is passed to the optics interface module 130 and hence to the microcontroller 128 and computer. The signal relating to the amount of fluorescence for each 360° rotation by the stepper motor B may be averaged whereby any variation around the circumference of the cartridge is averaged out. This provides an averaged signal for that particular vertical step. The process is repeated for each vertical step. The averaged signals are then summed to provide a total signal for that particular test and that signal may be displayed on the display 121.

This sum then provides a calibrated initial figure corresponding to that particular amount of toxin.

The process that may then be repeated with a new cartridge 104 with toxin of indeterminate quantity, and by comparing the summed output signals, a quantitative measurement of the fluorescence and hence of the target compound or toxin may be determined.

Clearly, it may be preferred to calibrate the apparatus by carrying out the calibration process by using two or more known amounts of toxin.

The invention is not restricted to the details of the foregoing examples.

In an alternative arrangement, in the place of a fluorescing target, there may be provided a non-fluorescent target compound which is measured by fluorescence quenching. Here a fluorophore—a fluorescent moiety—is incorporated into the polymer on which the target is adsorbed and the amount of fluorescence quenching (i.e. reduction of fluorescent radiation in the region of the target), which is caused by the target compound adsorbed onto the polymer, is measured. In this case, the amount of quenching is proportional to the amount of target compound.

The fluorescence may be transmitted from the sample cartridge to the detection unit by optical fibres.

The detector may comprise an image sensor in the form of a charge-coupled device (CCD), or CCD array.

The detector may comprise an image sensor in the form of an active pixel sensor (APS) consisting of an integrated circuit containing an array of pixels, each containing a photodetector as well as three or more transistors.

The detector may comprise an image sensor in the form of a linear photodiode.

The invention claimed is:

1. Apparatus for the detection or determination of a target comprising a target compound, a derivatised target compound or target compound-stimulated moiety, said apparatus comprising:
    means for mounting a sample cartridge, which sample cartridge comprises a packing or coating capable of immobilising or isolating the target in a layer or band,
    an excitation unit for emitting radiation that excites fluorescent radiation in the target,
    a detection unit that is sensitive to said fluorescence, and
    means for scanning the target with the detection unit, said means for scanning including
        means for relatively moving the mounting means and the detection unit whereby the fluorescent radiation from the target may be sensed,
        said means for relatively moving the mounting means and the detection unit comprising
            means for relatively moving the mounting means and the detection unit in such a manner as to scan the detection unit past all of the target,
    whereby the extent of the fluorescing target and the total fluorescence may be determined.

2. Apparatus according to claim 1, in which said target obscures said emitted fluorescent radiation.

3. Apparatus according to claim 1, in which the means for relatively moving the mounting means and the detection unit comprises:
    means for relatively moving the mounting means and the detection unit in a linear direction, and
    means for relatively rotating the mounting means and the detection unit.

4. Apparatus according to claim 3, in which the means for relatively moving the mounting means and the detection unit comprises a screw-threaded rod which is driven by an actuator motor.

5. Apparatus according to claim 3, in which the means for relatively moving the mounting means and the detection unit comprises a first stepper motor for relatively moving the mounting means and the detection unit in a linear direction and a second stepper motor for relatively rotating the mounting means and the detection unit.

6. Apparatus according to claim 1, further comprising a processing unit that converts the output of the detector unit into a readable value related to the amount of target compound immobilised in the layer or band.

7. Apparatus according to claim 1, further comprising a power source for one of the excitation unit and the detection unit.

8. Apparatus according to claim 1, in which the excitation unit comprises a light source and an excitation filter.

9. Apparatus according to claim 8, in which the light source comprises a continuously or intermittently driven xenon lamp.

10. Apparatus according to claim 8, in which the light source comprises a continuously or intermittently driven light emitting diode 11. Apparatus according to claim 1, in which the detection unit comprises a photodiode and a radiation filter.

12. Apparatus according to claim 11, in which the radiation filter comprises
    a plurality of radiation filters which allow different wavelengths to pass, and
    means for relatively moving the radiation filters and the photodiode or holder so as to bring each filter individually into the optical path between the holder and the photodiode.

13. Apparatus according to claim 11, in which the plurality of radiation filters comprise filter components of a filter wheel in which the filter components are individually brought into the optical path between the holder and the photodiode on rotation of the wheel.

14. Apparatus according to claim 11, in which the plurality of radiation filters is provided by different areas of a radiation filter.

15. Apparatus according to claim 1, in which the sample holder is rotatable with respect to the excitation unit and the detector unit.

16. Apparatus according to claim 1, in which the sample holder is movable normal to the plane of the excitation unit and the detector unit.

17. Apparatus according to claim 1, in which the sample comprises a cartridge packed with a molecularly printed polymer that is a selective adsorbent for the target.

18. Apparatus according to claim 17, in which the cartridge is a rod coated with the adsorbent for the target.

19. Apparatus according to claim 17, in which the cartridge is a column packed with a mineral adsorbent for the target.

20. Apparatus according to claim 1, in which the sample comprises a cartridge packed with a non-molecularly printed polymer that is a selective adsorbent for the target.

21. Apparatus according to claim 1, in which the components are mounted on a common staging and/or incorporated in a housing.

22. Apparatus according to claim 10 in which the plurality of filter wavelengths is provided by a monochromator.

23. Apparatus according to claim 1, where the fluorescence is transmitted from the sample cartridge to the detection unit by optical fibres.

24. Apparatus according to claim 1, wherein the detector unit is an image sensor in the form of a charge-coupled device (CCD), or CCD array.

25. Apparatus according to claim 1, where the detector unit is an image sensor in the form of an active pixel sensor (APS)

consisting of an integrated circuit containing an array of pixels, each containing a photodetector as well as three or more transistors 26. Apparatus according to claim 1, wherein the detector unit comprises an image sensor in the form of a linear photodiode.

27. Apparatus according to claim 1, wherein said layer or band is immobilized said sample cartridge.

28. Apparatus of claim 1, wherein said means for scanning comprises means for scanning above the band or layer, across the band or layer, and below the band or layer.

29. Apparatus of claim 1, wherein said means for scanning comprises means for scanning across a first band or layer and a second band or layer underneath said first band or layer.

30. Apparatus for the detection or determination of a target comprising a target compound, a derivatised target compound or target compound-stimulated moiety, said apparatus comprising:
    means for mounting a sample cartridge, which sample cartridge comprises a packing or coating capable of immobilising or isolating the target in a layer or band,
    an excitation unit for emitting radiation that excites fluorescent radiation in the target,
    a detection unit that is sensitive to said fluorescence, and
    means for scanning the target with the detection unit, said means for scanning including
        means for relatively moving the mounting means and the detection unit whereby the fluorescent radiation from the target may be sensed,
        said means for relatively moving the mounting means and the detection unit comprising
            means for relatively moving the mounting means and the detection unit in such a manner as to scan the detection unit past all of the target,
    whereby the extent of the fluorescing target and the total fluorescence may be determined,
    wherein the means for mounting the sample comprises a tubular support mounted in a support platform for the excitation unit and detection unit, and a support plate positioned below the tubular support to support the lower end of a cartridge located in the tubular support.

31. Apparatus according to claim 30, in which the tubular support
    is mounted in the plane of the excitation unit and the detector unit and
    has a first aperture through which a sample is exposed to radiation from the excitation unit and a second aperture through which fluorescence is observed by the detection unit.

32. Apparatus according to claim 30, in which the support plate
    is rotatable with respect to the tubular support and
    includes means for gripping the end of a supported cartridge.

33. Apparatus according to claim 30, in which the support plate is movable vertically with respect to the tubular support.

34. Apparatus according to claim 33, in which the cartridge is a tube or cuvette coated internally with the adsorbent for the target.

35. Apparatus according to claim 30, in which the support plate is mounted on a screw-threaded rod by which the support plate is rotatable and movable vertically with respect to the tubular support and the support plate includes means for gripping an end of a supported cartridge.

* * * * *